United States Patent [19]
deBear

[11] Patent Number: 5,391,128
[45] Date of Patent: Feb. 21, 1995

[54] OBJECT DELIVERY EXERCISE SYSTEM AND METHOD

[75] Inventor: Patricia C. deBear, Royal Oak, Mich.

[73] Assignee: Rahabilitation Institute of Michigan, Detroit, Mich.

[21] Appl. No.: 94,813

[22] Filed: Jul. 20, 1993

Related U.S. Application Data

[63] Continuation of Ser. No. 711,677, Jun. 6, 1991, abandoned.

[51] Int. Cl.⁶ .............................................. A63B 24/00
[52] U.S. Cl. ...................................... 482/4; 482/901; 601/23; 364/413.27; 901/31
[58] Field of Search .................... 482/1, 4-8, 482/111, 901-904; 128/25 R, 25 B; 364/413.02, 413.27, 551.01; 901/31; 414/744.6, 744.8; 601/23; 119/29

[56] References Cited

U.S. PATENT DOCUMENTS

| | | | |
|---|---|---|---|
| 4,235,437 | 11/1980 | Ruis et al. | 482/5 |
| 4,471,957 | 9/1984 | Engalitcheff, Jr. | 482/5 |
| 4,847,764 | 7/1989 | Halvorson | 364/413.02 |
| 4,882,677 | 11/1989 | Curran | 364/413.02 |
| 4,885,687 | 12/1989 | Carey | 364/413.02 |
| 4,933,873 | 6/1990 | Kaufman et al. | 364/413.02 |
| 4,936,299 | 6/1990 | Erlandson | 128/25 R |
| 5,186,695 | 2/1993 | Mangseth et al. | 482/902 X |

Primary Examiner—Stephen R. Crow
Assistant Examiner—Joe H. Cheng
Attorney, Agent, or Firm—Dykema Gossett

[57] ABSTRACT

A method and apparatus 10 are disclosed for allowing exercise of an appendage of patient 22 by means of a series of objects 42. More specifically, patient 22 is directed to receive or grasp a series of objects 42 in a manner which will exercise the impaired appendage and which will provide statistical data to a trained occupational therapist and which will enable the therapist to gauge the current dysfunction of the affected appendage as well as to track improvement over a series of exercises.

47 Claims, 7 Drawing Sheets

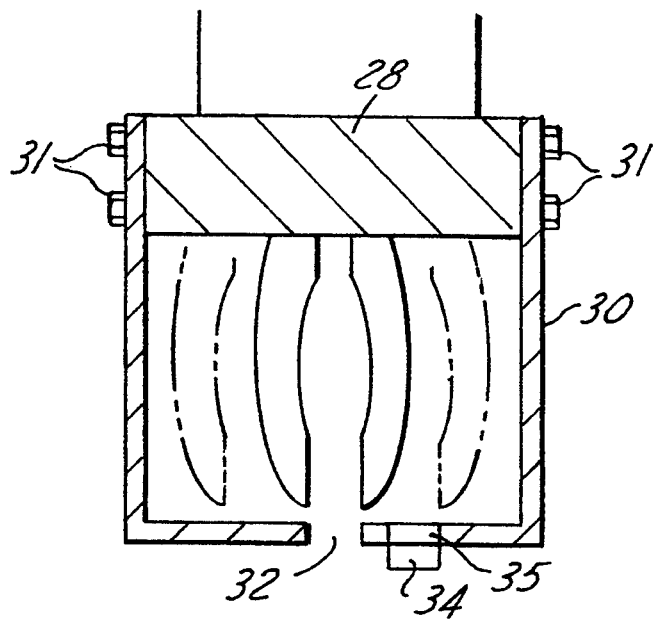
FIG.4
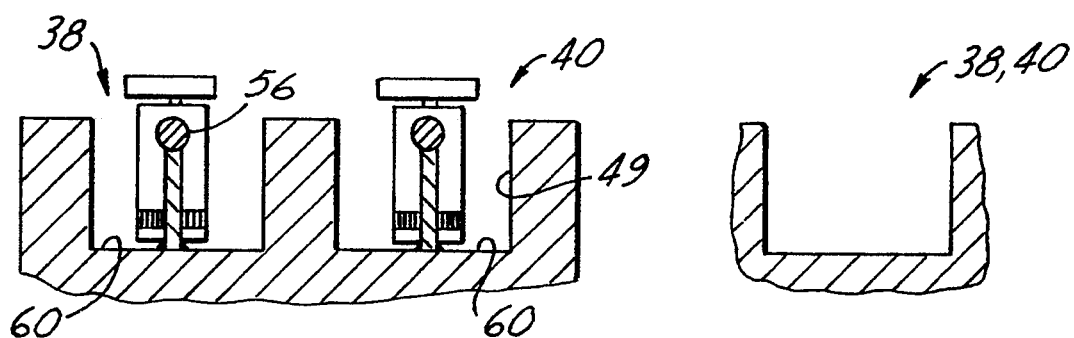
FIG.5
FIG.6
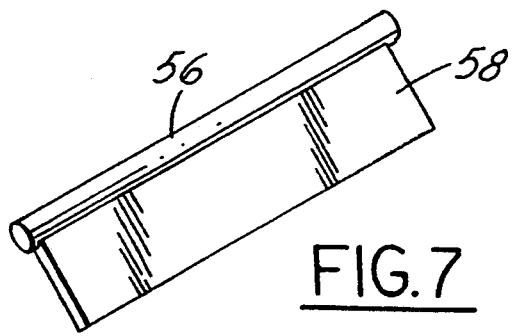
FIG.7
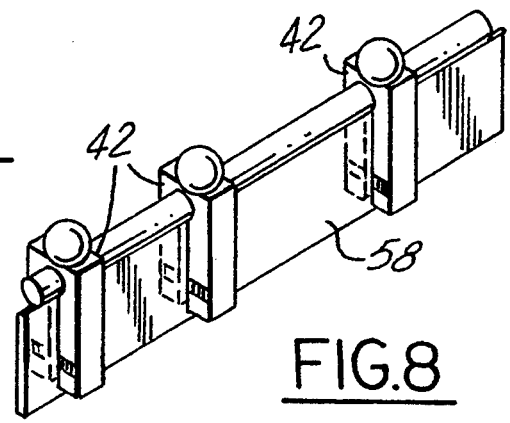
FIG.8

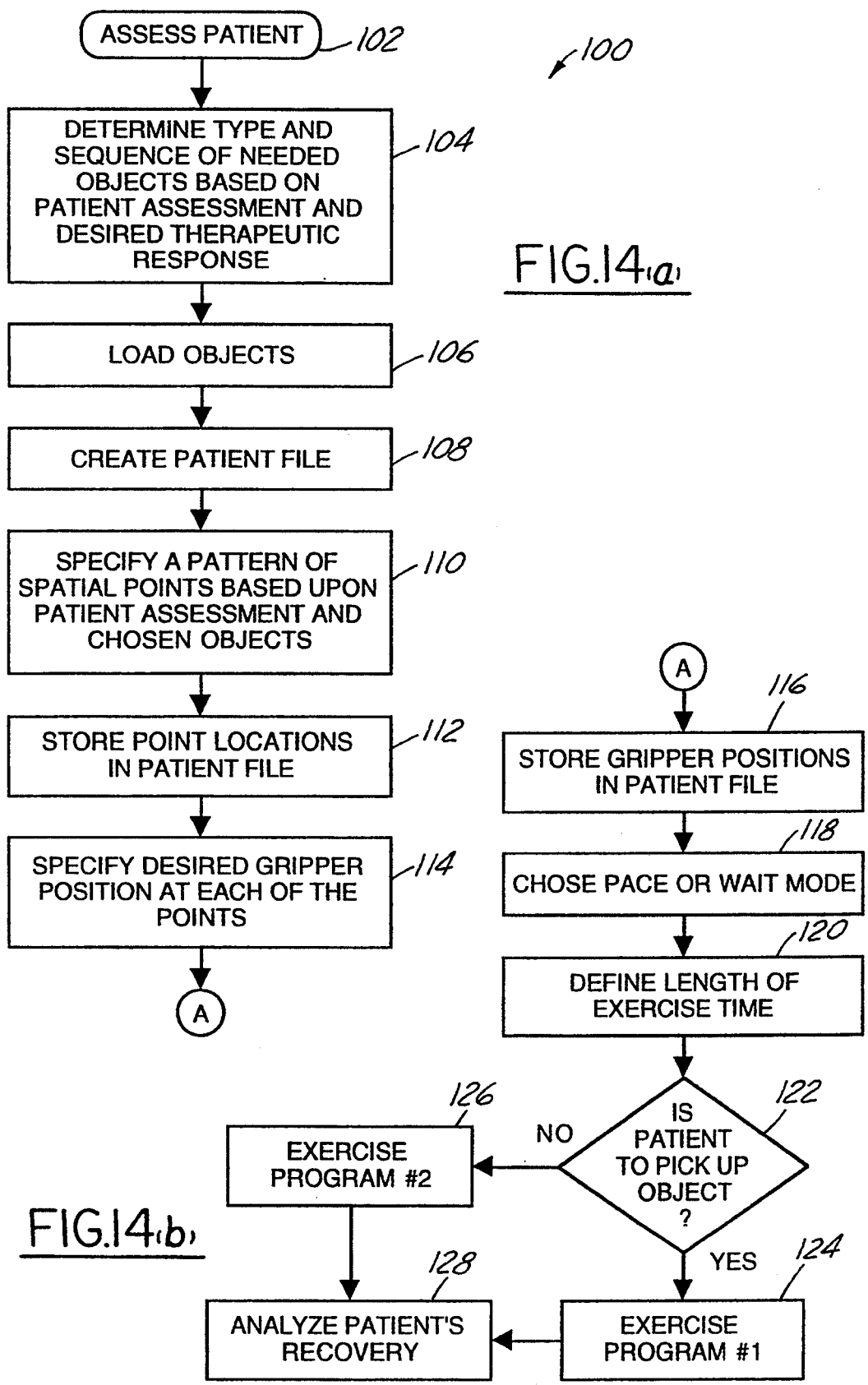

OBJECT DELIVERY EXERCISE SYSTEM AND METHOD

This is a continuation of application Ser. No. 07/711,677, filed on Jun. 6, 1991, now abandoned.

FIELD OF THE INVENTION

This invention generally relates to an object delivery system and, more particularly, to a method and an apparatus for therapeutically exercising a patient by requiring the patient to grasp a series of pre-defined objects, each having a certain therapeutic shape associated therewith, and to deliver these objects to a robot receptor positioned at a certain location relative to the patient or to an object receptacle.

DISCUSSION

Thousands of people are annually affected by injuries and disease which impair or limit hand, arm, or other appendage functionality. Examples of such injuries or diseases include multiple sclerosis, arthritis, quadriplegia, polyneuropathy, and traumatic brain or burn injuries. Regaining appendage functionality usually requires that the patients undergo extensive therapy, including a series of exercises which require the use and exercise of the various muscles comprising the affected appendages. Such exercises strengthen the appendage, thereby preventing further dysfunction and also increase overall fine and gross motor mobility thereby allowing the patients to actually improve overall appendage functionality.

Normally, these exercises require an occupational or physical therapist to define the type and amount of the needed exercise based upon each individual patient's condition. Moreover, the therapist normally participates and cooperates with the patient during the defined exercise program in order to ensure the correct completion of the exercise routine and to determine the patient's condition and progress.

One disadvantage of this prior arrangement is that both occupational and physical therapists are generally in short supply making it both difficult and costly for patients to participate in these exercise programs. Moreover, even if patients are fortunate enough to be able to participate in such programs, the patients' progress is still limited by the relatively short exercise periods available, again due to the large patient work load and short therapist supply.

SUMMARY OF THE INVENTION

It is therefore a primary object of this invention to provide a method and apparatus for exercising an impaired appendage or limb, including an arm or hand, effective to strengthen the exercised appendage and to increase fine and gross motor functions of the exercised appendage.

It is another object of this invention to provide a method and apparatus which is adapted to provide one of a multitude of exercises which are effective to exercise an impaired appendage.

It is yet a further object of this invention to provide a method and apparatus for allowing a patient's appendage to be exercised without the presence of a trained therapist during the entire exercise sequence.

It is another object of this invention to provide a method and apparatus for exercising an impaired appendage and for compiling statistical information on the exercised appendage which may be used to determine the relative dysfunction of the exercised limb and the overall improvement due to the exercise routine.

It is yet another object of this invention to provide a method and apparatus for exercising impaired limbs and appendages in various states and having various types of dysfunction.

According to a first aspect of this invention, a patient is assessed and, based upon this assessment, a series of uniquely shaped objects is selected in order to exercise a dysfunctional appendage. Each of these objects is sequentially delivered to the patient and the patient is directed to grasp and deliver each of the objects, by use of the dysfunctional appendage, to a robotic arm. The robot arm is sequentially placed a predefined spacial position relative to the patient. Both the type and number of dropped objects as well as the type and number of spatial positions at which the robot failed to receive an object are used to determine the relative dysfunction of the exercised appendage.

Further objects, features, and advantages of the invention will become apparent from a consideration of the following description and from the appended claims when taken in connection with the accompanying drawings.

BRIEF DESCRIPTION OF THE DRAWINGS

Various advantages of the present invention will become apparent to those skilled in the art by reading the following specification and by reference to the following drawings in which:

FIG. 4 is an exploded view of the robot gripper, taken in the direction of arrow 4 of FIG. 1;

FIG. 5 is a cross-sectional view of the object delivery apparatus shown in FIG. 1 and taken along line 5—5;

FIG. 6 is a view of the object delivery apparatus shown in FIG. 1 and taken in the direction of arrow 6;

FIG. 7 is a partial perspective view of the chute delivery rail shown in FIG. 1;

FIG. 8 is a partial perspective view of the chute delivery rail of FIG. 1, shown in inclined assembly relation with several objects;

FIGS. 14(a–b) are flow charts illustrating the general sequence of steps associated with the operation of system 10 of the preferred embodiment of this invention;

DETAILED DESCRIPTION OF THE INVENTION

Figure 1:
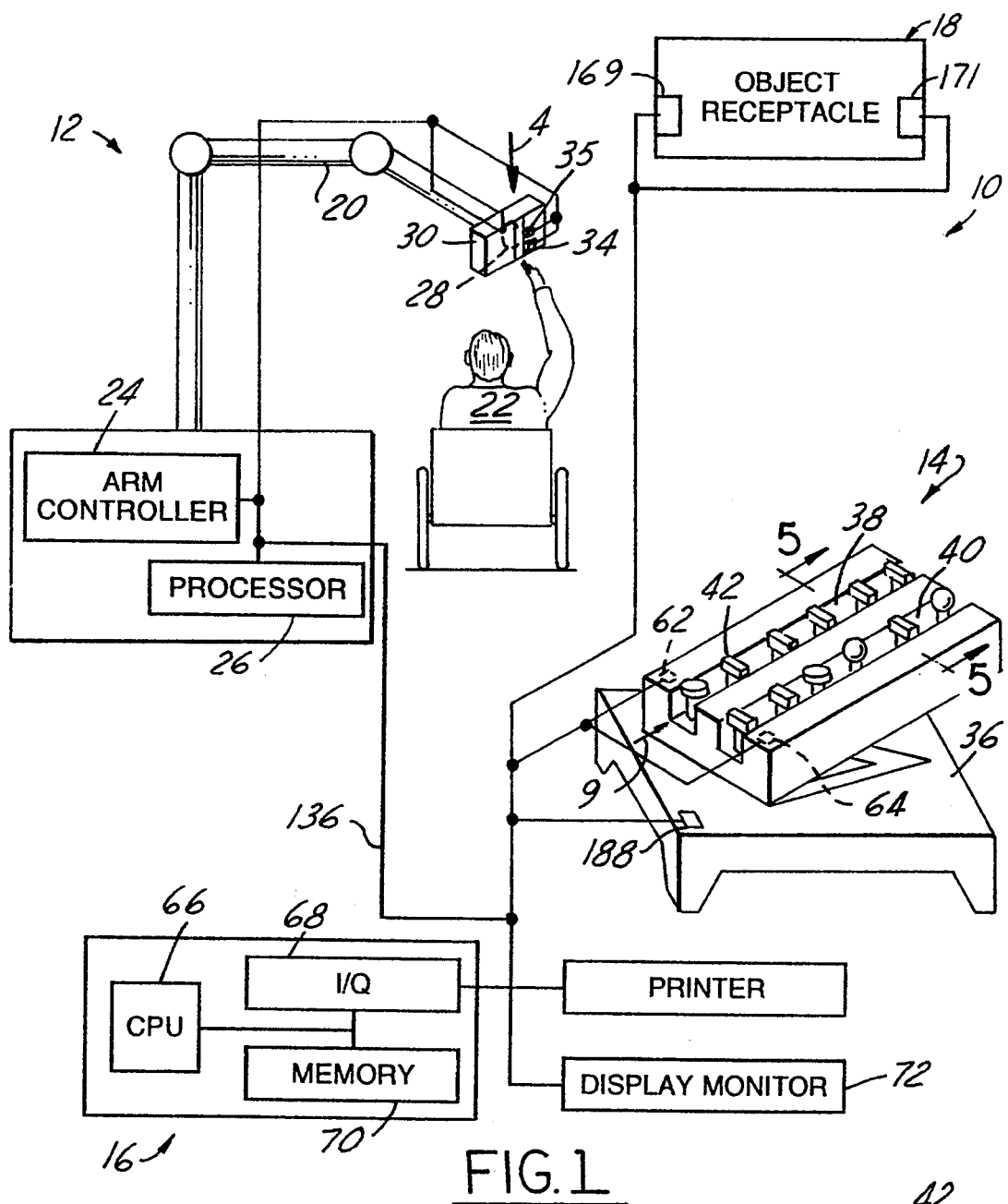
FIG. 1 is a block diagram of an object delivery system made according to the teachings of the preferred embodiment of this invention.

Referring now to FIG. 1, there is shown the object delivery system 10 of the preferred embodiment of this invention, including a robot 12, an object delivery apparatus 14, a computer 16, and an object receptacle 18.

Specifically, robot 12 includes an arm 20 which is capable of being selectively placed in close proximity to a patient 22 and which is further adapted to selectively and sequentially move to a pre-defined series of spatial points, proximate to patient 22. Such selective and sequential movement is usually accomplished in response to commands or movement of actuation arm controller 24. Typically, arm controller 24 comprises a series of servo motors which are under the control of processor 26 and which are specifically configured to selectively move arm 20 to a specific location in response to electrical signals received from processor 26.

Robot 12 further includes a gripper 28, coupled to controller 24 and processor 26, which is movable between a first open position and a second closed and object grasping position, as shown in FIG. 4. Moreover, gripper 28 is also pivotable about its point of attachment to arm 20. Accordingly, gripper 28 may selectively occupy a substantially vertical position (shown in FIG. 1), a substantially horizontal position (shown in FIG. 4), or substantially any angular position between the two illustrated positions. In practice, gripper 28 assumes an angle and either the open or closed position in response to electrical signals emanating from processor 26. In the preferred embodiment of this invention, gripper 28 is placed at the end of arm 20 and is adapted to selectively receive various objects from patient 22 or to grasp and hold objects from apparatus 14 and to allow these objects to be fetched by patient 22.

Moreover, robot 12 further includes, in the preferred embodiment of this invention, a clear acrylic box 30 which is attached to gripper 28 by means of bolts 31 (see FIG. 4) and which is adapted to substantially surround and contain gripper 28. Box 30 further has a fissure or longitudinal opening 32 which is aligned with gripper 28 so as to allow an object to be inserted therethrough and to allow the inserted object to be selectively gripped by gripper 28.

Box 30 also includes a motion detector 34 which is adapted to detect the presence of an object within fissure 32 and to generate an electronic signal to processor 26 in response to the detected object. Further, box 30 includes a bar code reader 35 adapted to read bar coded information residing on objects inserted into opening 32 and to transmit this information to processor 26 and to computer 16.

Specifically, box 30 is configured to prevent an inserted object from exerting a damaging amount of upward or downward force on gripper 28. Such prevention is due to the fact that the force is absorbed by box 30 before being imparted to gripper 28. The transparent nature of box 30 further provides a positive feedback to patient 22 by allowing the patient to actually see the object being inserted into the gripper 28.

Apparatus 14 includes a movable table 36 which is movable from a first horizontal and non-operative position to a second operable inclined position (shown in FIG. 1) and which further includes delivery chutes 38 and 40, each of which is adapted to slidably receive exercise objects 42.

Figure 2:
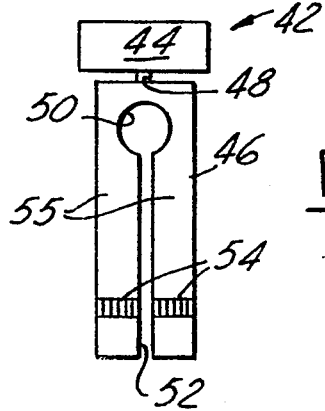
FIG. 2 is a front view of an object, used by the preferred embodiment of this invention and shown in assembly relation with a delivery base.
Figure 3:
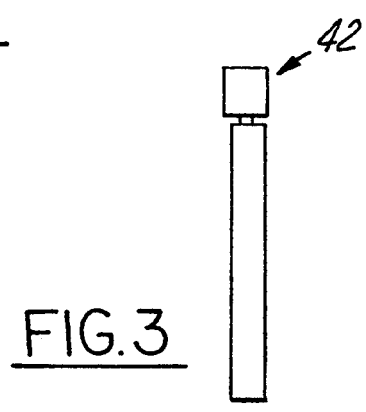
FIG. 3 is a side view of the object and delivery base shown in FIG. 2.

As shown in FIGS. 2 and 3, each object 42 includes a top patient-grasping portion 44 affixed to a base 46 by means of a screw 48 or other usual affixing means. In practice several different uniquely shaped top portions 44 are utilized, within system 10, in order to allow a variety of exercises to be tailored to meet a wide range of patient needs. Although many types of objects may be used within system 10, the preferred embodiment of this invention utilizes the following twelve shapes which are detailed in the table below:

TABLE 1

| PATIENT EXERCISE OBJECTS | | | |
| --- | --- | --- | --- |
| Object | Preferred Size | Pinch-Grasp that is Exercised | Functional Purpose |
| Ball | 3 inches | Spherical Grasp | Develops power grasp by incorporating substantially all of the finger and thumb movements |
| Doorknob | standard round size of lightweight construction | Spherical Grasp | Develops power grasp by incorporating substantially all of the finger and thumb movements |
| Cone | 2½ inch diameter base | Tone inhibitor Grasp | Helps to normalize abnormal muscle tone in the hand and develops power grasp by incorporating substantially all of the finger and thumb movements |
| Plastic Cup | 3 inch diameter | Cylindrical Grasp | Develops power grasp by incorporating substantially all of the finger and thumb movements |
| Bicycle Handle | standard | Cylindrical Grasp | Develops power grasp by incorporating substantially all of the finger and thumb movements |
| Drawer Handle | ½-¾ inch diameter | Cylindrical Grasp | Develops power grasp by incorporating substantially all of the finger and thumb movements |
| Key | standard key with large base | Lateral pinch | Develops fine manipulation prehension patterns by incorporating thumb opposition arrangement |
| Credit Card or equivalent shape | standard | Lateral pinch | Develops fine manipulation prehension patterns by incorporating thumb opposition arrangement |
| Cube | 1 inch | Three point opposition pinch | Develops fine manipulation prehension |

TABLE 1-continued

| | PATIENT EXERCISE OBJECTS | | |
|---|---|---|---|
| Object | Preferred Size | Pinch-Grasp that is Exercised | Functional Purpose |
| Ball | 1 inch | Three point opposition pinch | patterns by incorporating thumb opposition arrangement Develops fine manipulation prehension patterns by incorporating thumb opposition arrangement |
| Nail | finish nail or a sturdy box nail | Two point pinch | Develops fine manipulation prehension patterns by incorporating thumb opposition arrangement |
| Paperclip | large | Two point pinch | Develops fine manipulation prehension patterns by incorporating thumb opposition arrangement |

In the preferred embodiment of this invention, each of the patient grasping portions 44 reside upon a base 46 having substantially the same shape and size. In one embodiment, base is formed of resilient plastic and is of a general rectangular shape configured to be easily insertable within opening 32 and grasped by gripper 28. Moreover, base 46 has a round opening 50 in communication with a longitudinal slit 52. Each of the bases 46 also have substantially identical bar code encoding stripes 54 on each side of slit 52, each of which uniquely identify the respective object 42. It should be realized by one of ordinary skill in the art that stripes 54 may also be placed on sides 55 to ensure the identification of portion 46 in a variety of positions of object placement positions.

Referring now to FIGS. 1, 5, 6, 7 and 8 it is seen that each chute 38, 40 includes a round metal rod 56 longitudinally disposed within each of the respective chutes and attached to a longitudinally disposed metal partition member 58 which is welded along the bottom 60 of each of the chutes 38, 40.

Specifically, in the preferred embodiment of this invention, rod 56 is disposed within channels 38, 40 such that it resides substantially within the middle of each of the channels. In the preferred embodiment of this invention, rod 56 and metal sheet 58 traverse all but a small portion at each end of chute 38, 40. Moreover, each chute 38, 40, of the preferred embodiment of this invention, is configured to have substantially open ends, as shown in FIG. 6.

Each of the bases 46 is adapted to receive rod 56 within opening 50. Specifically, each object 42 is placed upon rod 56 by forcing slit 52 to become wider while concomitantly pushing rod 56 into the widening space of slit 52 thereby forcing rod 56 to occupy space 50. After each of the members 42 is placed upon rod 56, apparatus 14 is tilted to the position shown in FIG. 1 and each of the objects 42 is made, by gravity, to downwardly traverse rod 56 until reaching the bottom of each of the individual channels 38, 40. Because of the frictional engagement between rod 56 and each of the members 42, none of the members 42 will fall off of the rod 56 until actually picked up by either robot 12 or by patient 22. Alternatively, the diameter of rod 56 may be increased at its downward end to further ensure adequate opposition to the tendency of objects 42 to fall off the rod.

Figure 10:
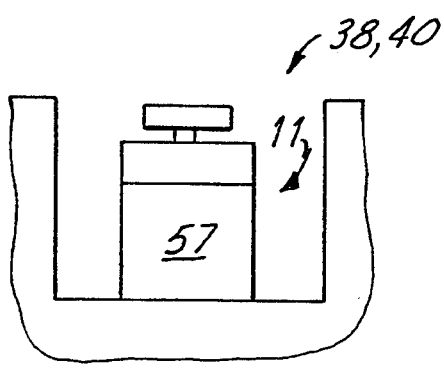
FIG. 10 is a view of one of the chutes of FIG. 1, taken in the direction of arrow 9 according to a third embodiment of this invention.
Figure 11:
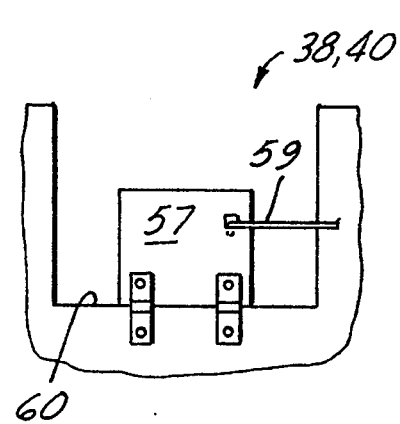
FIG. 11 is a view of the chute shown in FIG. 10 taken in the direction of arrow 11.

To ensure that none of the members 42 will fall off of rod 56, a third embodiment of this invention (shown in FIGS. 10 and 11) utilizes a blocking gate 57 at the object delivery (i.e. downward) end of each chute 38, 40. As shown, gate 57 is hingedly coupled to bottom portion 60 so as to be movable between a first downward position and a second upward and object blocking position. Such hinged coupling allows this chute end to be remotely placed from patient 22 (i.e. reconfigured as the upper end) and to allow objects 42 to loaded therethrough thereby increasing the versatility of chute 38, 40. Due to this hinged coupling arrangement, a hook 59 is needed to tightly secure gate 57 within chute 38, 40 thereby preventing any of the objects 42 from escaping.

Figure 12:
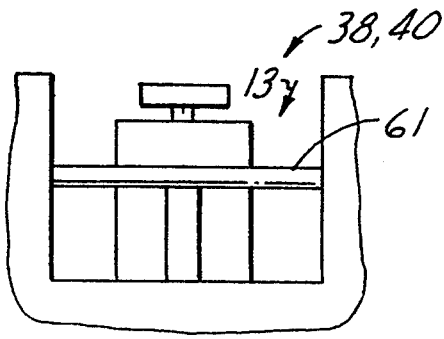
FIG. 12 is a view of one of the chutes of Figure 1, taken in the direction of arrow 9 according to a fourth embodiment of this invention.
Figure 13:
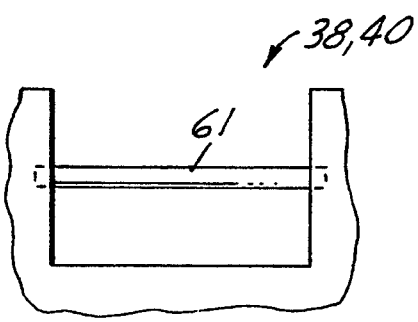
FIG. 13 is a view of the chute shown in FIG. 12, taken in the direction of arrow 13.

In a fourth embodiment of this invention, a bar 61 is coupled across each of the chutes 38, 40 (as shown in FIGS. 12, 13) thereby preventing objects 42 from prematurely leaving the individual chutes 38, 40.

Figure 9:
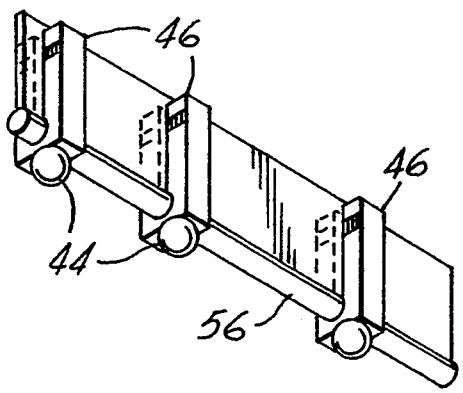
FIG. 9 is a partial perspective view of the chute delivery rail of FIG. 1, shown in inclined assembly relation with several objects according to a second embodiment of this invention.

In yet another embodiment of this invention (as shown in FIG. 9), the upward end of each chute 38, 40 is closed and rod 56 is removably secured to the closed upward end after objects 42 have been loaded on the rod 56. Such loading is effective to place base portion 46 upward and top portion 44 downward in order to allow robot 12 (more particularly gripper 28) to grasp and hold each object 42 by means of bases 46. As before, gravity will force each object 42 down rod 56 until reaching the end of the rod where they will be selectively removed, in a manner to be described. Moreover, portions 46 are supported by the sidewalls 49 of each chute 38, 40 thereby being prevented from falling to either side as they traverse down rod 56.

Alternatively, one of ordinary skill in the art will realize that the rod assembly of the first embodiment (shown in FIG. 8) may simply be rotated (once loaded) to achieve the same objective as shown in FIG. 9. Such rotation may be achieved within each chute 38, 40 by removably securing portion 58 to bottom portion 60.

As seen in FIG. 1, apparatus 14 further includes bar code readers 62, 64 which are adapted to read bar code stripe 54 from each of the objects 42 as they reach the bottom of chute 38 and 40. As also shown in FIG. 1, computer 16 includes a central processing unit 66 which is adapted to receive application software and to generate signals to the appropriate portion of system 10 in response to the received software. Computer 16 further includes an input/output portion 68 and a memory portion 70 which are both in communication with central processor 66 and which respectively allow data to be input and output from computer 16 and which allow data to be stored therein. Further, computer 16 includes a display monitor 72 which is electronically coupled to central processing unit 66 and which allows various stored and acquired data, as well as portions of the application software to be displayed to a user of system 10. Moreover, computer 16 includes a printer 74, coupled to input/output portion 68, which is adapted to accept data from central processing unit 66 and/or from memory 70 and to print the received data for later use by a user of system 10.

Referring now to FIGS. 14(a-b), there is shown a flow chart 100 illustrating the general sequence of steps associated with the operation of system 10 by a system operator. Specifically, flow chart 100 includes an initial step 102 in which an occupational therapist assesses patient 22 in order to determine the specific dysfunctions associated with the appendage to be exercised. It should be realized by one of ordinary skill in the art that the following discussion describes the exercise of a hand but that any other appendage, such as a leg, may also be exercised in substantially the same manner as described below.

Step 102 is followed by step 104 in which the occupational or physical therapist determines the type and sequence of needed objects 42 based upon the assessment in step 102, the desired therapeutic response, and the geometric configuration of top portions 44. More particularly, step 104 is performed by use of occupational or physical therapeutic knowledge known to those skilled in the occupational or physical therapeutic art.

Step 104 is followed by step 106 in which the sequence of objects, specified in step 104, are loaded, in the previously described manner, onto the rod 56, from the upward end of each chute 38, 40. That is, the first object to be received by patient 22 is loaded first while the last object to be received is loaded last. Moreover, if it is desired that the patient pick up the object 42 and deliver it to robot 12, the objects are loaded in the aforedescribed manner shown in FIG. 3. Alternatively, if it is desired that robot 12 fetch the objects 42 and deliver them or allow them to be fetched by patient 22, the objects, in step 106, are loaded in the aforedescribed manner in which base 46 is placed upward. One embodiment of this upward placement is shown in FIG. 9 and was also earlier described. Step 106 is followed by step 108 in which a system user specifies the patient 22 to be exercised and creates a patient file within computer 16. The patient file, in the preferred embodiment of this invention, is adapted to store data associated with that patient's exercise routine.

Step 108 is followed by step 110 in which a system user specifies a specific pattern and sequence of spatial points based upon the patient assessment and chosen sequence of objects. It should be apparent to one of ordinary skills in the art that these points may be created for each exercise routine or alternatively, specific patterns of points may be predetermined and stored within memory 70 and may be reused in step 110. Such groups of points moreover, may be identified with specific types of dysfunctions and accordingly may be easily used for general types of patients having particular and previously identified dysfunction.

Step 112 follows step 110 in which the specified and desired spatial point locations are stored under a selected exercise title in the patient file, of step 108. Such storing in the preferred embodiment of this invention is accomplished by use of memory 70.

Step 114 follows step 112 in which the system operator specifies and stores, within memory 70, the desired angular gripper position associated with each of the previously specified points. Step 118 follows step 116 and requires the system operator to chose either a "pace" or a "wait" mode. Specifically, a "pace" mode is defined to be a mode in which the arm 20 waits for a predefined period of time at a previously specified spatial point and moves to the next sequentially defined spatial point if it does not receive one of the objects 42 during the specified period of time. In the "wait" mode, the robot 12 continually waits at a spatial point for receipt object 42 and does not move until actually receiving an object, or is specifically directed to do so by patient 22. Step 120 follows step 118 in which the system operator determines the length of total exercise time to be given to patient 22 based upon the patient's assessment and the operator' workload.

Step 124, defining a first exercise program, follows step 120 only if patient 22 is to pick up the objects 42 while step 126, defining a second exercise program, follows step 120 only if the robot is to hand the objects to patient 22. Step 128 follows both steps 124 and 126 and requires an analysis of the patient's recovery.

Figure 15A:
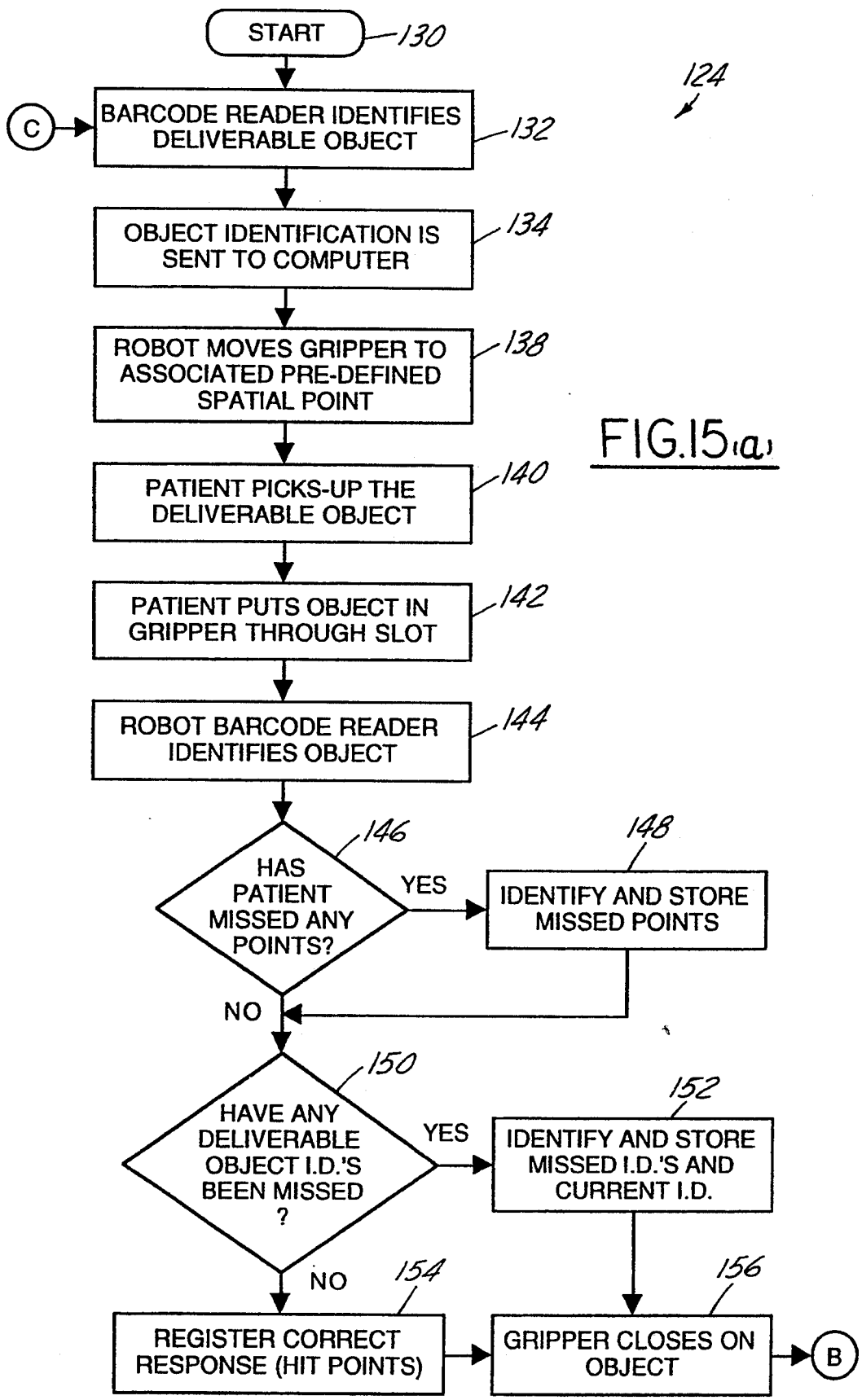
FIGS. 15(a-b) are flow charts showing the sequence of steps associated with Exercise Program I, shown in FIG. 14(b)
Figure 15B:
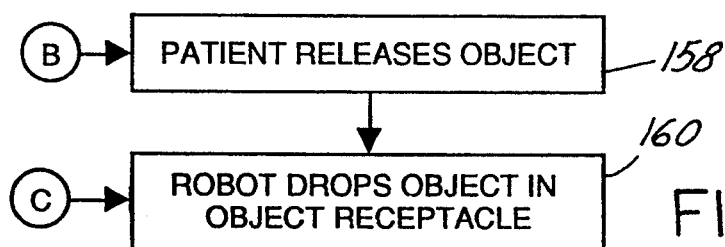

Referring now to FIGS. 15(a–b) there is shown a sequence of steps associated with Exercise Program I of step 124, shown in FIG. 14(b). Specifically, step 124 includes an initial step 130 in which a start command is given by a system operator by means of monitor 72 to the central processing unit 66. After receipt of this command, processing unit 66 sends a signal to bar code readers 62 and 64 allowing one of them to read the bar code information included on stripe 54 of a single one of the objects 42, currently located at the bottom of one of the channels 38 or 40.

Step 132 follows step 130 in which one of the readers 62, 64 identifies the object 42 located at the bottom of one of the channels 38, &0. Step 134 follows step 132 in which the activated bar code reader 62, 64 transmits this object identification to the central processing unit 66 by means of bus 136 and portion 68. Step 138 follows step 134 in which robot 12 moves gripper 28 to the first associated predefined spatial point which was created in step 110 and to the associated angular gripper position. If this is the first object which has been read, gripper 28 is moved to the first point. Alternatively, gripper 28, in step 138, is moved to the next sequential spatial point, in the sequence of the previously defined points.

Step 140 follows step 138 in which patient 22 picks up the deliverable object 42 whose tar code information on stripe 54 has just been read. Step 142 follows step 140 in which the patient 22 puts object 42 into gripper 28 through the opening 32. In step 144 bar code reader 35 identifies the object 42 which has just been placed through opening 32 by reading the bar code stripe 54.

Step 146 follows step 144 in which central processing unit 66 determines whether any previous spatial points had been missed by the patient. That is, if the robot was in a "pace" mode and moved to this spatial point (i.e. the point at which the robot currently received the object), it is possible that there were previous spatial points which the patient failed to present an object to the gripper 28. Alternatively, if robot 12 was in the "wait" mode and directed to move to the current object reception point by patient 22 (in a manner to be explained) a missed point would arise. If such missed points exist, processing unit 66, in the preferred embodiment of this invention, would store these points before allowing arm 20 to move to the next sequential point. If the missed points have already been stored, they are not stored again. Therefore, step 146 is followed by step 148 only if missed points exist and, in this step, central processing unit 66 stores the previously identified missed points. Step 150 follows both steps 146 and 148 and requires the central processing unit 66 to determine if any deliverable objects 42 had been missed or dropped.

That is, during system operation it is possible that patient 22 could have dropped some of the objects 42 that were obtained from chutes 38 or 40. Since each of the objects 42 received by patient 22 had their associated bar code stripe 54 read and stored by central processing unit 66, a simple comparison between each of the stored bar code identification information and the bar code identification information actually read by bar code reader 34 yields a set of objects which had been picked up by patient 22 but not delivered to robot 12. In step 152, these identified objects are stored and tagged as missed or dropped objects. In step 152, the current bar code identification information associated with the object 42 which has just been placed into opening 32 is also stored. Alternatively, step 150 is followed by step 154 in which central processing unit 66 is directed to register a correct response or a "hit" point associated with the placement of the correct object at the correct spatial point. Step 156 follows step 152 and 154 in which gripper 28 closes upon the object 42 which has just placed into opening 32.

Step 158 follows step 156 in which the patient is directed or told to release the object 42 and step 160 follows step 168 in which robot 12 is directed to drop object 42 into object receptacle 18. Step 160 is followed by steps 132-160 as previously described. Moreover, it should be realized that receptacle 18 included at least two bar code readers 169, 171 which are coupled to bus 136 and adapted to read stripe 54 of every object 42 which is placed within the receptacle. This information is sent to processor 66 in order to ensure that robot 12 correctly places these objects 42 into receptacle 18 for later use.

Figure 16A:
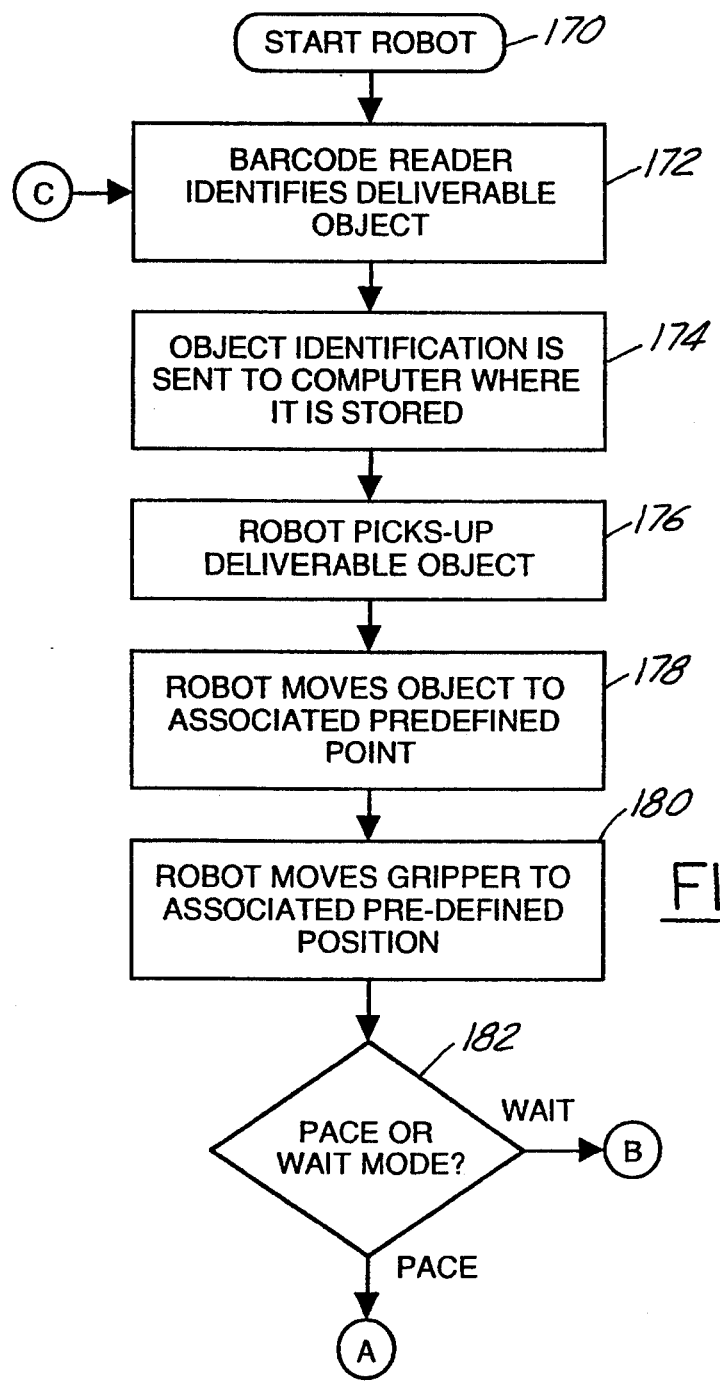
FIGS. 16(a-c) are flow charts illustrating the sequence of steps associated with Exercise Program II, shown in FIG. 14(b).
Figures 16B, 16C:
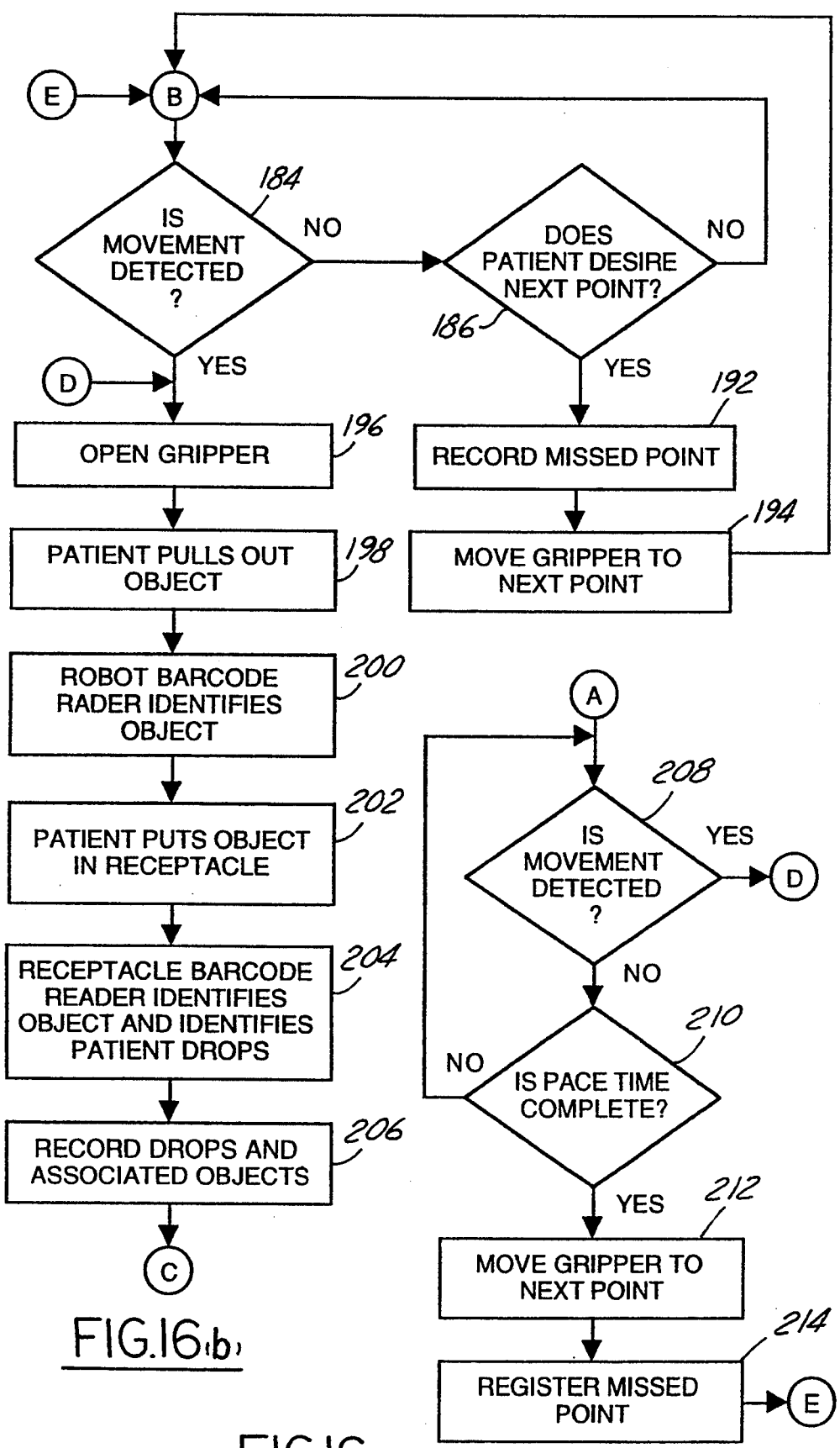

Referring now to FIGS. 16(a-c) there is shown a sequence of steps associated with Exercise Program II, shown in step 126 of FIG. 14(b). Specifically, step 126 includes an initial step 170 in which robot processor 26 receives a start command from central processing unit 66 by means of a signal on bus 136. Step 172 follows step 170 in which one of the bar code readers 62 or 64 is directed to read one of the objects 42 currently residing at the bottom of respective channel 38, 40.

Step 174 follows step 172 in which the object identification information is sent to the central processing unit 66, by means of bus 136, where it is stored in memory 70. Step 176 follows step 174 in which robot 12 is directed to pick up the identified object 42. This direction is achieved by control signals emanating from central processing unit 66, along bus 136, which are eventually received by processor 26. After receiving such control signals, processor 26 activates arm controller 24 and directs gripper 28 in the appropriate manner.

Step 178 follows step 176 in which robot 12, and more particularly arm 20, is directed to move the object 42 to the associated predefined spatial point of step 110. It should be realized by one of ordinary skill in the art that if this was the first object 42 that was picked up, the spatial point, associated with step 178, would be the first point that was previously defined. Alternatively, the spatial point, utilized in step 178, would be the next sequential point in the pattern specified in step 110. Step 180 follows step 178 in which robot 12 is directed to move gripper 28 to the associated predefined angular position associated with step 114 and the previously defined spatial point.

Step 182 follows step 180 in which the central processing unit 66 must determine whether a "pace" or a "wait" mode is desired. If a "wait" mode is desired, step 182 is followed by step 184 in which movement sensor 35 is queried by processor 26 in order to determine whether movement or motion has been detected through opening 32. If such movement has not been detected, step 184 is followed by step 186 in which central processing unit 66 determines whether patient 22 wants or desires to move the robot 20 to the next spatial point. In practice, patient 22 may specify or move arm 20 to the next spatial point by means of movement control button 188 which is coupled to the central processing unit 66 by means of bus 136. If such movement is not desired, step 186 is followed by step 184.

If in step 186, patient 22 desires to move gripper 28 to the next predefined spatial point, step 186 is followed by step 192. Specifically, step 192 requires that the central processing unit 66 record the current spatial point as being a "missed" point and then enter step 194 in which gripper 28 is moved to the next sequential spatial point and given the associated angular gripper position. Step 194 is followed by step 184.

Step 184 is followed by step 196 if movement has been detected by movement sensor 35. In step 196, gripper 28 is opened by means of control signals emanating from processor 26. Step 198 follows step 196 in which patient 22 is directed to pull out the object 42 which is currently in gripper 28. Step 200 follows step 198 in which the bar code reader 35 identifies the object 42 which is to be pulled out from gripper 28 by patient 22.

Step 202 follows step 200 in which patient 22 puts the recently "pulled out" object 42 into the receptacle 18. Step 204 follows step 202 in which bar code readers 169, 171 read the bar code identification information on stripe 54, as the object is put into receptacle 18. This information is transmitted to central processing unit 66 by means of bus 136. Step 206 follows step 204 in which central processing unit 66 records an object drop and the actual associated dropped object if, in step 204 no such bar code information is read. That is, an absence of information emanating from readers 169, 171 during a period in which an object 42 is to be placed within receptacle 18, implies that the object 42 has been dropped. Step 206 is followed by step 172.

If in step 182, a "pace" mode is selected, step 182 is followed by step 208 in which central processing unit 66 determined whether motion sensor 35 has detected the entry of an object 42 into opening 32. If such movement is detected, step 208 is followed by step 196. If such movement has not been detected, step 208 is followed by step 210 in which central processing unit 66 must determine whether the previously defined "pace" time is complete. If such "pace" time has not been complete, then step 210 is followed by step 208.

Alternatively, step 210 is followed by step 212 in which gripper 28 is moved to the next sequential point in the pattern of spatial points defined in step 110. Step 214 is followed by step 212 in which the central processing unit 66 is directed to register the previous spatial point as a "miss" point. Step 214 is followed by step 184.

It should be apparent to one of ordinary skill in the art that the sequence of steps associated with the previously described FIGS. 14(a-b), 15(a-b), and 16(a-c) may not be fixed and that these aforedescribed steps may be accomplished in any order desired by a user of system 10 and that this rearrangement is considered to be within the scope of this invention. Further it should be understood by one of ordinary skill in the art that since human movement occurs in saggital, transverse, frontal, and diagonal planes that the use of the grasps incorporated with this robot allows an individual to learn grasping and manipulation of everyday objects in a variety of these useful movement plane patterns.

Therefore, it should be further apparent to one of ordinary skill in the art that by properly specifying the types and sequence of objects along with properly specifying the necessary spatial points, one may therapeutically exercise a patient 22 (and more particularly a patient's appendage such as an arm or hand) in a manner in which relatively swift progress may be made to the impaired appendage and which acts to prevent further impairment.

Additionally, it should be realized that once an occupational or physical therapist has assessed the appendage impairment and defined the needed exercise, spatial points, and object sequence, the actual exercise or sequence of exercises may be accomplished by a relatively unskilled technician, rather than a highly skilled occupational or physical therapist. This, therefore, is clearly advantageous since this reduces the actual cost of these exercises, allows each of the patients to exercise more frequently, and allows a greater number of patients to have access to needed therapeutic exercises. Further, by properly storing both the number and type of spatial points that the patient 22 failed to reach, the number and type of objects which the patient dropped, and the sequence of these missed points and dropped objects within the total exercise pattern, a trained occupational therapist may recognize not only the current state of the impaired appendage but also can track the appendage improvement over a period of exercise time. Therefore, according to the preferred embodiment of this invention, this stored information may be both displayed onto monitor 72 as well as printed on printer 74. More particularly, the actual kinds of errors within the exercise sequence might allow a trained occupational therapist to gage endurance, tolerance, or relative attentiveness of the patient 22 while the type and amount of missed points will allow the occupational therapist to determine the range of motion, reach, strength, and overall gross motor skills associated with patient 22. Moreover, the number and type of dropped objects 42 will lo enable a trained occupational therapist to determine the fine motor skills which are currently associated with that patient 22 as well as any sort of improvement over a period of exercise time associated therewith. Therefore, in step 128, the acquired data from each of these exercise patterns, for a given patient, may be analyzed in order to determine the aforedescribed characteristics.

It is to be understood that the invention is not limited to the exact construction or method illustrated and described above, but the various changes and modifications may be made without departing from the spirit and scope of the invention as defined in the following claims.

I claim:

1. A patient exercise system, comprising:
  object delivery means for automatically providing an object to be fetched by a patient;
  reception means, movable to a certain first one of a plurality of spatial positions, for receiving said object from said patient upon movement to said certain first one of said plurality of spatial positions and for selectively grasping and moving said object to a certain second one of said plurality of spatial positions and for allowing said patient to fetch said object when said object has been placed at said certain second one of said plurality of spatial positions; and
  movement control means for controlling movement of said reception means and for selectively moving said reception means to said certain second one of said plurality of spatial positions.

2. The patient exercise system of claim 1 wherein said reception means comprises a robot.

3. The patient exercise system of claim 1 wherein said object delivery means comprises a chute having a planar member longitudinally disposed therein; and
  means, having a first portion adapted to attach to said object and a second portion adapted to slidably attach to said planar member, for allowing said object to move from a first position within said chute to a second position in close proximity to said patient.

4. A patient exercise system of claim 1, further comprising reception movement means for allowing said patient to move said reception means from said certain first one of said plurality of spatial positions to any other of said plurality of spatial positions.

5. The patient exercise system of claim 1, wherein said movement control means further moves said reception means to a certain third one of said plurality of spatial positions after a predetermined period of time has elapsed.

6. The patient exercise system of claim 1 wherein said object comprises a ball.

7. The patient exercise system of claim 1 wherein said object comprises a key.

8. The patient exercise system of claim 1 wherein said object comprises a doorknob.

9. The patient exercise system of claim 1 wherein said object comprises a nail.

10. The patient exercise system of claim 1 wherein said object comprises a cube.

11. The patient exercise system of claim 1 wherein said object comprises a cone.

12. The patient exercise system of claim 1 wherein said object comprises a drinking glass.

13. The patient exercise system of claim 1 wherein said object comprises a bicycle handle.

14. The patient exercise system of claim 1 wherein said object comprises a credit card.

15. The patient exercise system of claim 1 wherein said object comprises a paper clip.

16. A patient exercise system comprising:
  means for automatically arranging a plurality of objects in a certain order and for sequentially providing each of said plurality of objects to be fetched by a patient according to said certain order;
  reception means for sequentially receiving each of said objects from said patient;
  reception movement means for allowing said patient to move said reception means from a certain first one of a plurality of spatial positions to any other of said plurality of spatial positions; and
  movement control means for controlling said reception movement means and for selectively moving said reception means to said certain first one and said any other of said plurality of spatial positions.

17. The patient exercise system of claim 16 wherein said reception means comprises a robot.

18. The patient exercise system of claim 16, wherein said means for automatically arranging said plurality of objects in said certain order and for sequentially providing each of said plurality of objects to be moved by said patient according to said certain order comprises:

a chute having a planar member longitudinally disposed therein; and means, having a first portion adapted to attach to one of said plurality of objects and a second portion adapted to slidably attach to said planar member, for allowing said object to move from a first position within said chute to a second position in close proximity to said patient.

19. The patient exercise system of claim 16 wherein said reception means comprises means for receiving each of said objects from said patient upon movement to said certain first one of said plurality of spatial positions and for electively grasping and moving each of said objects to a certain second one of said plurality of spatial positions and for allowing said patient to fetch each of said objects when each of said objects has been placed at a certain second one of said plurality of spatial positions.

20. The patient exercise system of claim 16 wherein said movement control means moves said reception means to a certain third one of said plurality of spatial positions after a predetermined period of time has elapsed.

21. The patient exercise system of claim 16 wherein said object comprises a ball.

22. The patient exercise system of claim 16 wherein said object comprises a key.

23. The patient exercise system of claim 16 wherein said object comprises a doorknob.

24. The patient exercise system of claim 16 wherein said object comprises a nail.

25. The patient exercise system of claim 16 wherein said object comprises a cube.

26. The patient exercise system of claim 16 wherein said object comprises a cone.

27. The patient exercise system of claim 16 wherein said object comprises a drinking glass.

28. The patient exercise system of claim 16 wherein said object comprises a bicycle handle.

29. The patient exercise system of claim 16 wherein said object comprises a credit card.

30. The patient exercise system of claim 16 wherein said object comprises a paper clip.

31. A method for exercising an appendage of a patient in a patient exercise system wherein said patient exercise system has an object delivery means for arranging and sequentially providing each of a plurality of objects to be fetched by a patient, reception means for sequentially receiving each of said objects from said patient and controls means coupled to said object delivery means and said reception means for moving said reception means to a certain one of a plurality of spatial positions, comprising the steps of:

specifying several objects that are to be grasped by an appendage of a patient;

arranging said specified objects in a certain order;

automatically delivering each of said objects to said patient according to said certain order from said object delivery means; and causing said patient to grasp said objects delivered from said reception means by use of said appendage and to move each of said delivered objects on said reception means to a predetermined spatial position.

32. The method of claim 31 further comprising the steps of assigning a unique predetermined spatial position to each of said delivered objects, respectively; and causing said patient to move each of said delivered objects to said unique predetermined respective spatial position.

33. The method of step 31 further comprising the step of defining at least one of said objects to be a ball.

34. The method of step 31 further comprising the step of defining at least one of said objects to be a key.

35. The method of step 31 further comprising the step of defining at least one of said objects to be a doorknob.

36. The method of step 31 further comprising the step of defining at least one of said objects to be a nail.

37. The method of step 31 further comprising the step of defining at least one of said objects to be a cube.

38. The method of step 31 further comprising the step of defining at least one of said objects to be a coil.

39. The method of step 31 further comprising the step of defining at least one of said objects to be a drinking glass.

40. The method of step 31 further comprising the step of defining at least one of said objects to be a bicycle handle.

41. The method of step 31 further comprising the step of defining at least one of said objects to be a credit card.

42. The method of step 31 further comprising the step of defining at least one of said objects to be a paper clip.

43. The method of claim 31 further comprising the step of defining said appendage to be a hand.

44. The method of claim 31 further comprising the step of defining said appendage to be an arm.

45. A patient exercise system comprising:

object delivery means for automatically and sequentially providing an object to be fetched by a patient;

reception means for receiving said fetched object from said patient including a movement controller for moving said reception means to a certain one of a plurality of spatial positions; and control means for automatically controlling said object delivery means and said reception means according to a selected exercise program.

46. A patient exercise system, comprising:

object delivery means for automatically providing an object to be fetched by a patient, wherein said object delivery means comprises a chute having a planar member longitudinally disposed therein and means, having a first portion adapted to attach to said object and a second portion adapted to slidably attach to said planar member, for allowing said object to move from a first position within said chute to a second position of close proximity to a patient;

reception means, movable to a certain first one of a plurality of spatial positions, for receiving said object from said patient upon movement to said certain first one of said plurality of spatial positions, for selectively grasping and moving said object to a certain second one of said plurality of spatial positions and for allowing said patient to fetch said object when said object has been placed at said certain second one of said plurality of spatial positions; and controller means, coupled to said object delivery means and to said reception means, for selectively moving said reception means to said certain first one and to said certain second one of said plurality of spatial positions.

47. A patient exercise system, comprising:

means for automatically arranging a plurality of objects in a certain order and for sequentially providing each of said plurality of objects to be fetched by a patient according to said certain order including a chute having a planar member longitudinally disposed therein, and means, having a first portion adapted to attach to one of said plurality of objects and a second portion adapted to slidably attach to said planar member, for allowing said object to move from a first position within said chute to a second position in close proximity to said patient;

reception means for sequentially receiving each of said objects from said patient; and movement control means for controlling movement of said reception means and for selectively moving said reception means to at least one of a plurality of spatial positions.

* * * * *